"(12) United States Patent
Richey et al.

(10) Patent No.: US 10,226,551 B2
(45) Date of Patent: Mar. 12, 2019

(54) APPARATUS AND METHODS FOR FOAM POSITIONER MANUFACTURE (71) Applicant: Cassemco, Inc., Cookeville, TN (US)

(72) Inventors: David Adam Richey, Cookeville, TN (US); John Thomas Nipper, Cookeville, TN (US)

(73) Assignee: Cassemco, Inc., Cookeville, TN (US)

( * ) Notice: Subject to any disclaimer, the term of this patent is extended or adjusted under 35 U.S.C. 154(b) by 614 days.

(21) Appl. No.: 14/951,027

(22) Filed: Nov. 24, 2015

(65) Prior Publication Data
US 2016/0143599 A1    May 26, 2016

Related U.S. Application Data (60) Provisional application No. 62/084,388, filed on Nov. 25, 2014.

(51) Int. Cl.
A61L 31/10    (2006.01)
A61L 31/14    (2006.01)
A61L 31/18    (2006.01)
A61B 6/04     (2006.01)

(52) U.S. Cl.
CPC ............ *A61L 31/10* (2013.01); *A61B 6/0442* (2013.01); *A61L 31/146* (2013.01); *A61L 31/18* (2013.01)

(58) Field of Classification Search
CPC ................ A61B 6/0442; A61B 5/0555; A61G 2210/50; A61G 13/1235; A61G 13/12; A61G 13/124; A61G 6/04; A61G 7/075; A47C 20/023
See application file for complete search history.

(56) References Cited

U.S. PATENT DOCUMENTS

| | | | | |
|---|---|---|---|---|
| 3,746,332 A | * | 7/1973 | Hakstian | A61F 5/37 5/647 |
| 4,270,235 A | * | 6/1981 | Gutmann | A61G 7/075 5/646 |
| 5,029,573 A | * | 7/1991 | Chow | A61B 1/317 600/104 |
| 5,327,912 A | * | 7/1994 | Melly | A61B 6/0421 128/878 |
| 5,971,006 A | * | 10/1999 | Seigerschmidt | A61G 7/05753 137/223 |
| 7,168,114 B1 | * | 1/2007 | Larenas | A61B 6/0421 5/632 |

(Continued)

*Primary Examiner* — Eric J Kurilla
(74) *Attorney, Agent, or Firm* — Hanley, Flight and Zimmerman, LLC (57) ABSTRACT Example positioning and/or support apparatus and associated methods of manufacture are disclosed and described herein. An example foam positioner device includes an outer profile formed at a first angle to support an anatomy, wherein the first angle is an angle other than ninety degrees and wherein the first angle divides the outer profile into at least a first portion and a second portion. The example device also includes a coating covering the outer profile to seal the device. An example method includes forming an outer profile of the device at a first angle to support an anatomy, wherein the first angle is an angle other than ninety degrees and wherein the first angle divides the outer profile of the device into at least a first portion and a second portion; and covering the outer profile with a covering to seal the outer profile of the foam positioner device.

20 Claims, 7 Drawing Sheets (56) References Cited

U.S. PATENT DOCUMENTS

| | | | | |
|---|---|---|---|---|
| D733,897 S | * | 7/2015 | Rossouw | D24/184 |
| 2009/0031499 A1 | * | 2/2009 | Mervar | A61G 7/075 5/647 |
| 2010/0281616 A1 | * | 11/2010 | Karlson | A47G 9/10 5/632 |
| 2011/0231995 A1 | * | 9/2011 | Sedillo | A61B 6/0421 5/601 |
| 2013/0064345 A1 | * | 3/2013 | Kaska | A61B 6/04 378/62 |
| 2013/0340171 A1 | * | 12/2013 | Oberst | A61G 7/075 5/630 |
| 2014/0031666 A1 | * | 1/2014 | Shaikh | A61B 6/04 600/407 |
| 2016/0174721 A1 | * | 6/2016 | Kubota | A47C 16/00 5/657 |
| 2017/0042339 A1 | * | 2/2017 | Monderine | A47C 27/14 |
| 2018/0104125 A1 | * | 4/2018 | Vahala | A61G 13/124 |

* cited by examiner

APPARATUS AND METHODS FOR FOAM POSITIONER MANUFACTURE

RELATED APPLICATION

This patent claims the benefit of U.S. Provisional Application Ser. No. 62/084,388, entitled "Apparatus and Methods for Foam Positioner Manufacture," which was filed on Nov. 25, 2014, and is hereby incorporated herein by reference in its entirety.

FIELD

The present field of invention relates to foam positioners, and more specifically to apparatus and methods to manufacture foam positioners at particular angles.

BACKGROUND

Foam positioners are used to help position, guide, or immobilize parts for imaging. However, current foam positioners are ineffective and introduce artifacts into a resulting image. These artifacts can lead to errors in image review. Current techniques have been ineffective in reducing or eliminating these artifacts.

BRIEF DESCRIPTION OF THE DRAWINGS

A clear conception of the advantages and features constituting the present invention, and of the construction and operation of typical mechanisms provided with the present invention, will become more readily apparent by referring to the exemplary, and therefore non-limiting, embodiments illustrated in the drawings and photos accompanying and forming a part of this specification, wherein like reference numerals designate the same elements in the several views, and in which.

DETAILED DESCRIPTION OF CERTAIN EMBODIMENTS

Before certain embodiments of the invention are explained in detail, it is to be understood that the invention is not limited in its application to the details of construction and the arrangement of the components set forth in the following description or illustrated in the drawings. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe example implementations and not to be taken as limiting on the scope of the subject matter described in this disclosure. The invention is capable of other embodiments and of being practiced or being carried out in various ways. Certain features from different aspects of the following description may be combined to form yet new aspects of the subject matter discussed below.

Also, it is to be understood that the phraseology and terminology used herein are for the purpose of description and should not be regarded as limiting. The use of "connected," "including," and "comprising" and variations thereof in the description and the claims is meant to encompass the items listed thereafter and equivalents thereof as well as additional items and equivalents thereof. When introducing elements of various embodiments of the present disclosure, the articles "a," "an," "the," and "said" are intended to mean that there are one or more of the elements.

Certain examples described and disclosed herein relate to foam positioners and foam positioner manufacture. Certain examples provide apparatus and methods for improved angle manufacture of foam positioners. Certain examples provide apparatus and methods to reduce or eliminate artifacts caused by foam positioners in imaging.

Hospitals, clinics, doctor's offices, and/or other facilities use imaging devices, such as x-ray imaging scanners, in fields such as radiology to look for abnormalities in bones and other parts of human and animal bodies. Imaging systems are also used in machine, food and packaging industries such as by employing x-ray scanners to identify foreign objects. To get a best image or view of an area of interest, a patient or object to be imaged is positioned with a foam support for comfort, to immobilize, and/or to optimize or otherwise improve quality and usability of a resulting image.

Unfortunately, prior foam supports appear as artifacts in the resulting image, rather than being "invisible" or radiolucent (e.g., permitting passage of radiant energy, such as x-ray, with little or no attenuation), whether formed using coated or non-coated foam. While attempts have been made to manufacture a foam support that is radiolucent while providing the same positionability, attempts using different designs and/or methods of applying a coating have failed until certain examples disclosed and described herein. For example, prior re-designs have changed functionality of the positioner such that it fails to provide proper support. Additionally, prior methods of coating result in a coating that is applied so thin that the product is not reusable after a few cleanings while also not being radiolucent in the first place.

While some non-coated supports can be provided as radiolucent, non-coated supports cannot be reused if blood, urine, and/or other fluid from a human or animal subject comes into contact with the foam. However, under current hospital and other standards, having support/positioner products that are reusable and have a radiolucent and cleanable exterior coating would be highly desirable.

Prior foam supports (e.g., positioning sponges) are manufactured with either a 90-degree angle or something close to vertical throughout the part. This 90-degree or close to vertical angle creates an angle perpendicular to an x-ray or other imaging device, which results in what appears to be a line in the resulting image, especially with respect to support/positioner products that have been coated and, as a result, have a "skin". The artifact line looks much like a fracture in a bone, and, therefore, gives technician a false reading. While this prior set is considered "industry standard", it creates a plurality of lines or artifacts in the resulting image and causes false notation of breaks or defects in an object being imaged.

In certain examples, a supportive structure provides support and optimal or improved positioning of an object to image while not compromising or reducing any compromise in functionality and clarity in a resulting image. Certain examples provide a support/positioning structure that provides support and positioning while also able to be cleaned and reused without showing lines or artifacts in the resulting image. Certain examples reduce or eliminate image artifacts due to a lack of perpendicular or near vertical lines in the positioner device.

In certain examples, a support/positioning part is formed of polyurethane foam, thermosetting polymer foam, thermoplastic polymer foam, soy-based foam, and/or other radiolucent foam (e.g., other open cell foam, closed cell foam, cross-link, foam, polyester, etc.) or similar material and is designed with no perpendicular or vertical angles when viewed with respect to a table or imaging device, such as an x-ray scanner, which is looking directly down or parallel to the table. In some examples, the imaging device views the support/positioning part from the side rather than from or in addition to a top down table view, so the desired line artifact to be removed is still perpendicular to the imaging device.

In certain examples, plastic can be used to form the support/positioner device. The design of the support/positioner component accounts for an intended purpose of the "positioner" (e.g., to position and/or support an object, such as a body part (e.g., a finger, hand, leg, head, etc.) and incorporates angles that create a non-visible line (e.g., 60 to 85 degrees, other angle less than 90 degrees, angle greater than 90 so as not to create a line for the imaging detector, etc.). Rather than a right or near vertical angle, forming the positioner from this new set of angles allows the part to be coated with a variety of materials, such as vinyl (e.g., liquid vinyl, vinyl paint, plasticizer, plastisol, polyvinyl chloride (PVC), latex, polyethylene, synthetic rubber, etc.) and/or other coating material to create a liquid-proof barrier over the positioner, while not compromising functionality and quality of the part or resulting image. The part can be coated using a hand spray, waterfall, robot application (e.g., robot spray, etc.), dipping, etc. Measurements are computed to use angles which will not cause edges or surfaces of the positioner to appear as artifacts in an obtained image. Once the positioner/support part is designed to remove all perpendicular angles and is tested to confirm proper functionality and radiolucency (e.g., by making and coating a sample part, by simulating operational characteristics and performance of the part, etc.), the part can be drawn for production on a variety of machines, for example.

For example, a schematic for a positioner/support device can be drawn as a computer aided design (CAD) file. A log, bun, or roll of material (e.g., foam, etc.) that will form a plurality of positioner/support parts is fed into a knife or machine cutter such as a profile cutter, etc. The profile cutter takes the input CAD file and follows instructions in the CAD file to cut a profile of the log, bun, or roll of material that will form a plurality of positioner/support parts. The profile cutter is then programmed to cut the log/roll of parts into individual parts of specified respective size(s) and angle(s). Alternatively or in addition, the parts can also be designed to be cut on a press, by routing, routing after freezing the material first, by a hand cut, by using jigs, water jet, hot wire, lasers, molded, etc. Once the parts are cut, the parts are then coated with a material that allows cleaning and reuse of the product. The coating process can be done several ways including but not limited to dipping, spraying, waterfall, rolling, transfers, etc. After all sides of the product have been coated and dried, the part is ready for use.

The product is used by placing the product on a table or other surface under or otherwise positioned with respect to an x-ray or other imaging device. In an example, if the product has been designed for a hand, then a subject places her or his hand on top of the positioner/support product. In some hand positioners, individual areas are formed on which the subject's finger(s) are rested. Once the hand is in position, an imaging technician can then take a "picture" or image of the hand. After use, the positioner/support product is wiped clean and set aside for the next use.

In another example, if a patient needs a body x-ray such as a spinal x-ray, for example, a 45-degree wedge positioner/support part is used in order to hold the patient in a correct position for the image to be obtained. The wedge support/positioner product is slid underneath the patient's body to hold the patient in place while the technician takes the image. Again, the device is removed when finished and wiped down to be ready for its next use. Other product configurations include, but are not limited to, limb/extremity holders and immobilizers, head holders and immobilizers, bolsters, pads, knee supports, finger blocks, head rests, various angled wedges, etc.

Figure 1:
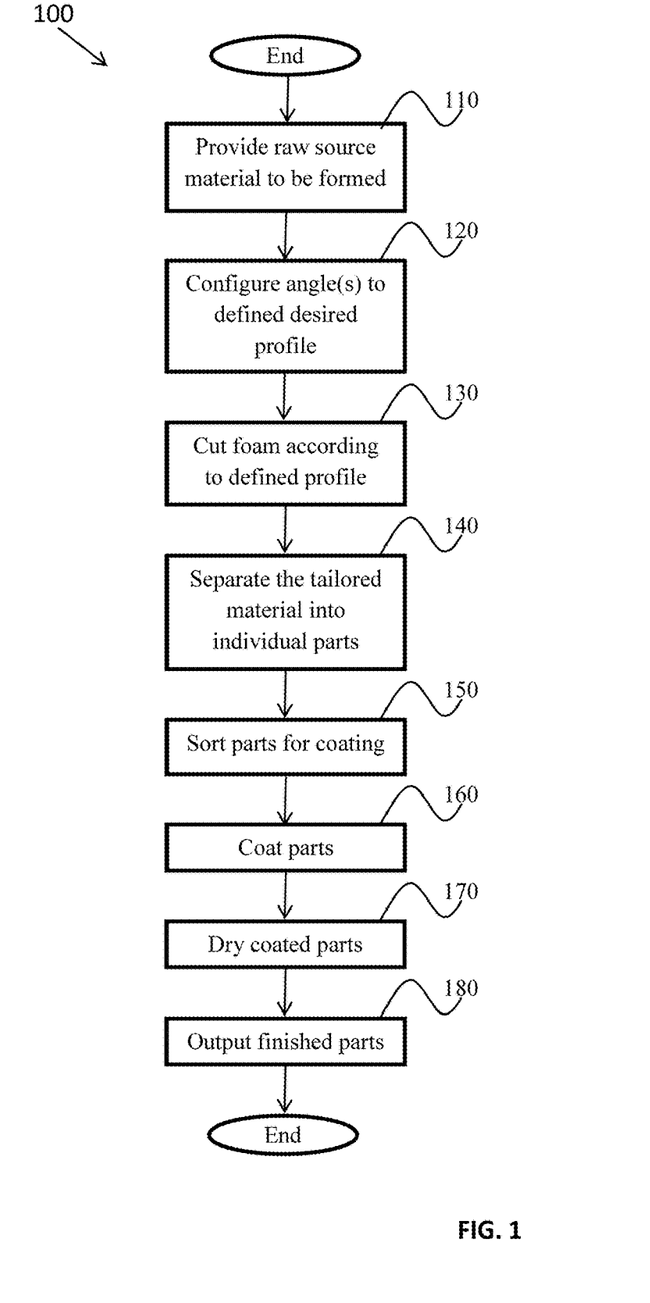
FIG. 1 illustrates an example process to manufacture foam positioning devices.

FIG. 1 illustrates an example process 100 to manufacture foam positioning devices. At block 110, material is provided to the process to form the foam positioning devices. For example, a bun, log, roll, or other mass of foam (e.g., polyurethane foam and/or other similar foam) is loaded into a processing machine to manufacture the foam positioning devices. The foam source material can be pushed, pulled, rolled, conveyed, injected, blown, flowed, and/or otherwise fed into the machine for processing.

At block 120, one or more angles are configured (e.g., 60-85 degrees, etc.) to define a desired outer profile of the resulting foam positioner. The angle(s) can be fixed or otherwise predefined, provided on a part-by-part or run-by-run basis, customized for a particular order, etc. In certain examples, parts can be custom designed. For example, a CAD file and/or other machine setting is configured to set the angle(s) at which the foam source material is to be cut and/or otherwise formed to set the desired exterior profile of the foam positioner product.

At block 130, the foam source material is cut to define the outer profile of the resulting foam positioner in the source material. The cutter follows preset angle(s) in one or more provided instruction or drawing files (e.g., CAD files) to cut an appropriate profile. For example, a knife, saw (e.g., vertical saw, band saw, etc.), profile cutter, die cutter, and/or other cutting tool is set to cut or carve at the specified angle or set of angles through the bun or block of foam source material.

At block 140, the tailored foam source material is then cut into separate pieces according to positioner part size and/or other dimension. For example, a profile cutter such as a Baumer™ and/or other band knife or similar cutting tool (e.g., by hand cut, round cut, compression cut, etc.) can be used to divide the foam source material into individual positioner parts. In certain examples, the foam source material is pressed (e.g., using a cutting press (referred to as a clicker) or other die cutter, etc.) as well as cut. In some examples, plastic material can be die cut using a press as well.

At block 150, the positioner parts are sorted for coating. For example, parts can be sorted by hand and/or sorted automatically by part, size, weight, and/or other criteria, etc. Parts can be separated using machinery to divide and organize a plurality of parts into a sequence for ease of coating. When sorted, the parts can be examined for consistency and accuracy to the provided design. Quality control/review can be facilitated manually and/or electronically based on weight, shape, dimension, etc.

At block 160, individual parts are coated. For example, a spray, dipping, waterfall, and/or other coating mechanism is provided to apply one or more coats of waterproofing and/or sealant (e.g., liquid vinyl, vinyl paint, plasticizer, plastisol, latex, etc.) to facilitate radiotranslucency, artifact reduction, cleanability, reproducibility, etc., of the positioner parts. Coating the positioner parts can be done to provide the parts with one or more properties including: radiolucent, anti-fungal, anti-bacterial, non-allergenic, flame retardant, self-deodorizing, stain-resistant, easy to clean, etc.

At block 170, the coated parts are dried. For example, blowing air, heat, and/or other air drying mechanism is provided to dry the coat(s) on the parts. In certain examples, parts are air dried before being ready for use/packaging.

At block 180, the finished parts are output for packaging and/or use. In certain examples, parts are kept in order so as to not mix up parts of different size and/or other configuration. Sorted parts are then moved to a packaging area to be placed in a bag with a label applied to each bagged part, and the bags are then placed in one or more boxes for shipping.

Thus, certain examples implement the example method 100 to form radiolucent, coated positioner parts that support a patient anatomy while reducing artifacts and/or other erroneous effects in an obtained medical image. Certain examples improve manufacturing of such positioner parts, operational effectiveness of such positioner parts, durability, and reproducibility of such positioner parts, etc.

Figure 2:
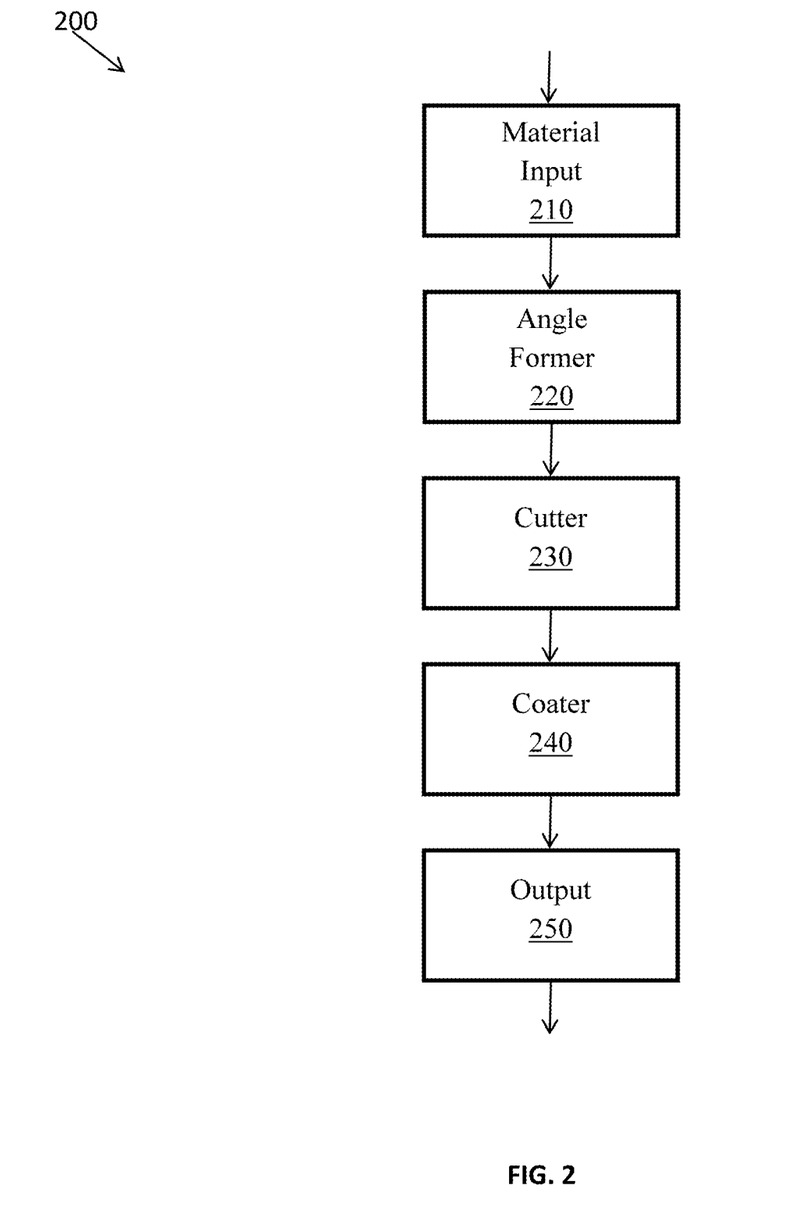
FIG. 2 illustrates an example system to manufacture foam positioner/support apparatus.

FIG. 2 illustrates an example system 200 to manufacture foam positioner/support apparatus. The example system 200 includes a material input 210, an angle former 220, a cutter 230, a coater 240, and an output 250. As described above, the material input 210 receives foam source material and arranges it for processing. The angle former 220 cuts and/or otherwise forms one or more desired (e.g., pre-programmed) angles into the foam source material. The cutter 230 then cuts the angled foam source material into individual positioner/support parts. The system 200 can be configured to provide parts in various shapes and/or sizes, for example. After the parts are separated, the coater 240 applies one or more layers of coating to seal and/or otherwise preserve the durable, radiolucent properties of the foam parts. The coated parts may be dried as part of the coating process and/or may be allowed to dry for a certain period of time after coating by the coater 240, for example. The output 250 then provides the finished parts for use, sorting, packaging, shipment, etc.

Figure 3A:
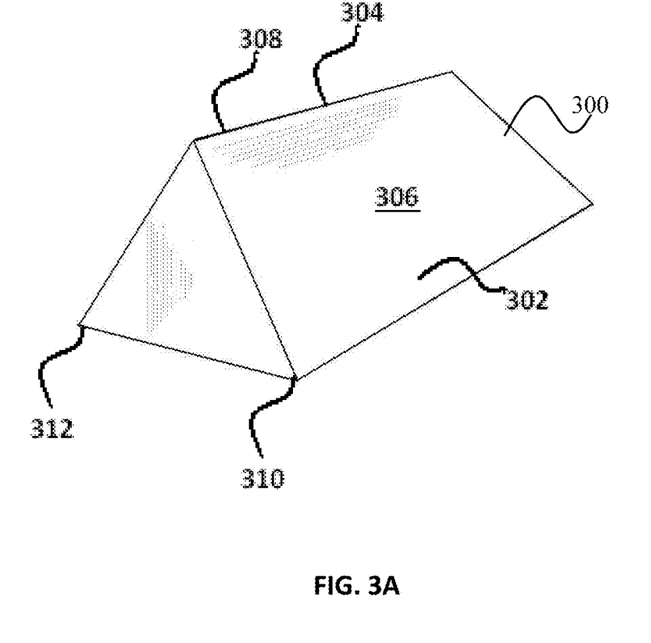
FIGS. 3A-3B show example foam positioners formed using process(es) and/or system(s) disclosed and described herein.

FIG. 3A shows an example foam positioner 300 formed using the process 100 and/or system 200 disclosed and described above. The wedge of FIG. 3A can be cut at a specified angle to reduce or eliminate image artifact when a patient anatomy resting on the positioner 300 is imaged by an imaging device (e.g., x-ray scanner, CT scanner, etc.). As shown in the example of FIG. 3A, the positioner 300 has an outer profile 302 formed at a first angle 304 to support a first anatomy. In certain examples, the first angle 304 is an angle other than ninety degrees (e.g., forty-five degrees, between sixty and eighty-five degrees, etc.), and the first angle divides the outer profile 302 of the device into at least a first portion 306 and a second portion 308. A coating (e.g., a radiolucent coating) covers the outer profile 302 to seal the outer profile 302 of the foam positioner device 300. The example positioner 300 shown in FIG. 3A includes additional angles 310, 312 that may or may not be the same as each other and/or the same as the first angle 304, for example.

Figure 3B:
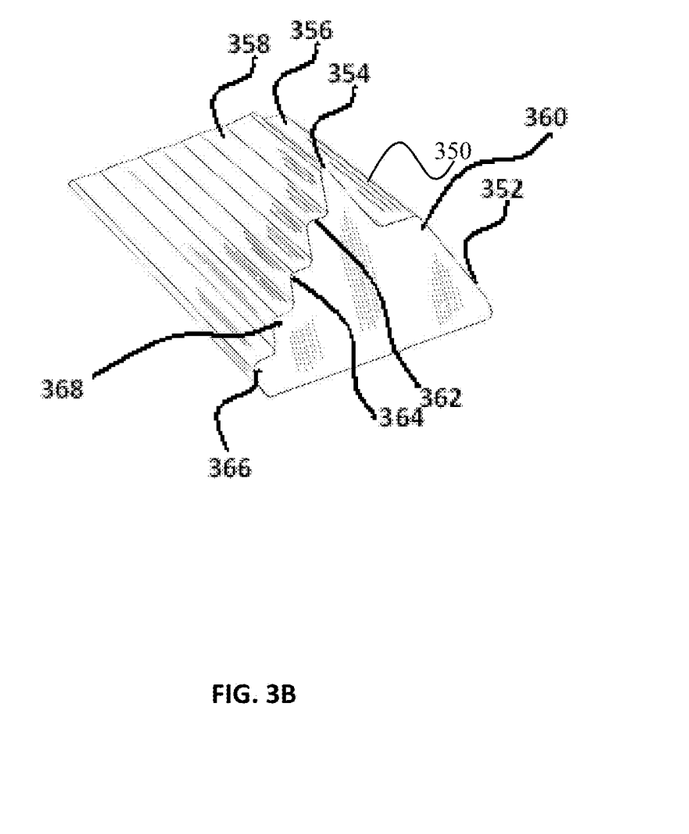

FIG. 3B shows another example foam positioner 350 formed using the process 100 and/or system 200 disclosed and described herein. The example positioner 350 provides a more complicated profile formed through specifying angles and cutting as disclosed and described above. The example positioner 350 allows a user to place his or her fingers on various levels (also referred to as areas or portions) formed at one or more angles of the positioner 350 to spread the fingers apart and render them stationary for an image to be obtained.

As shown in the example of FIG. 3B, the positioner 350 has an outer profile 352 formed at at least a first angle 354 to support a first anatomy. In certain examples, the first angle 354 is an angle other than ninety degrees (e.g., forty-five degrees, between sixty and eighty-five degrees, etc.), and the first angle 354 divides the outer profile 352 of the device into at least a first portion 356 and a second portion 358. A coating (e.g., a radiolucent coating) covers the outer profile 352 to seal the outer profile 352 of the foam positioner device 350. The example positioner 350 shown in FIG. 3B includes a plurality of additional angles 360-368 that may or may not be the same as each other and/or the same as the first angle 354, for example.

Figure 4A:
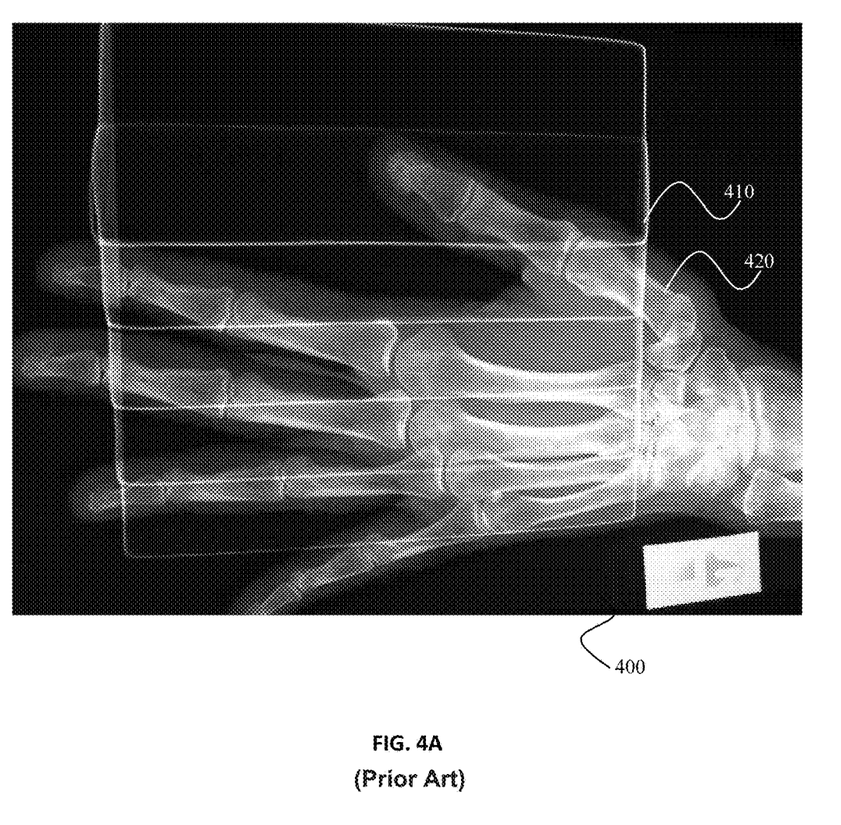
FIG. 4A shows an example x-ray image taken with a prior positioning device.

FIG. 4A shows an example x-ray image 400 taken with a prior positioning device. As shown in the image 400, a plurality of artifact lines 410 appear clearly and confusingly in the image 400. The artifact lines 410 are generated by the prior positioning device used to position the hand 420 for the image 400. The angles of the prior positioning device create lines 410 in the images 400 that cannot be distinguished from an anatomy of interest in the image 400, causing confusion and potential for misdiagnosis by a reviewing healthcare practitioner.

Figure 4B:
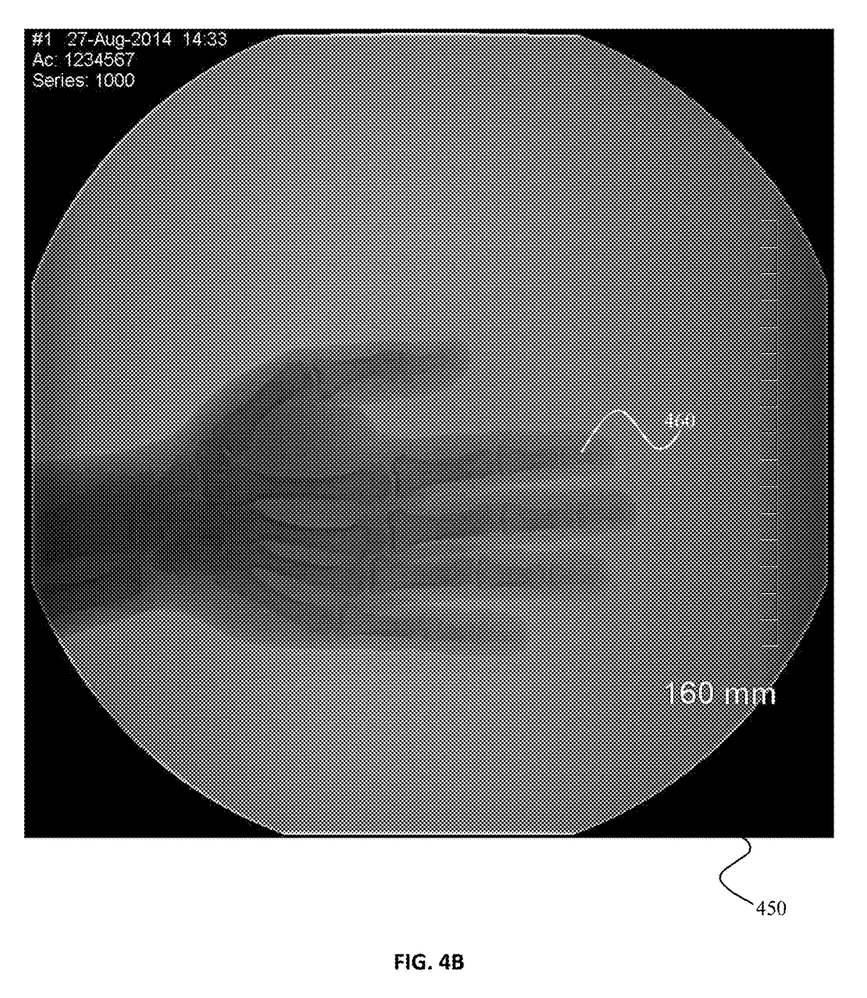
FIG. 4B shows an example x-ray image taken with a foam positioning device formed using process(es) and/or system(s) disclosed and described herein.

FIG. 4B shows an example x-ray image 450 taken with a foam positioning device, such as positioner 300, formed using the process 100 and/or system 200 disclosed and described herein. The example image 450 includes a subject hand 460 but, in stark contrast to the prior image 400, no artifacts can be seen as a result of using the improved positioner rather than a prior positioning device.

Figure 4C:
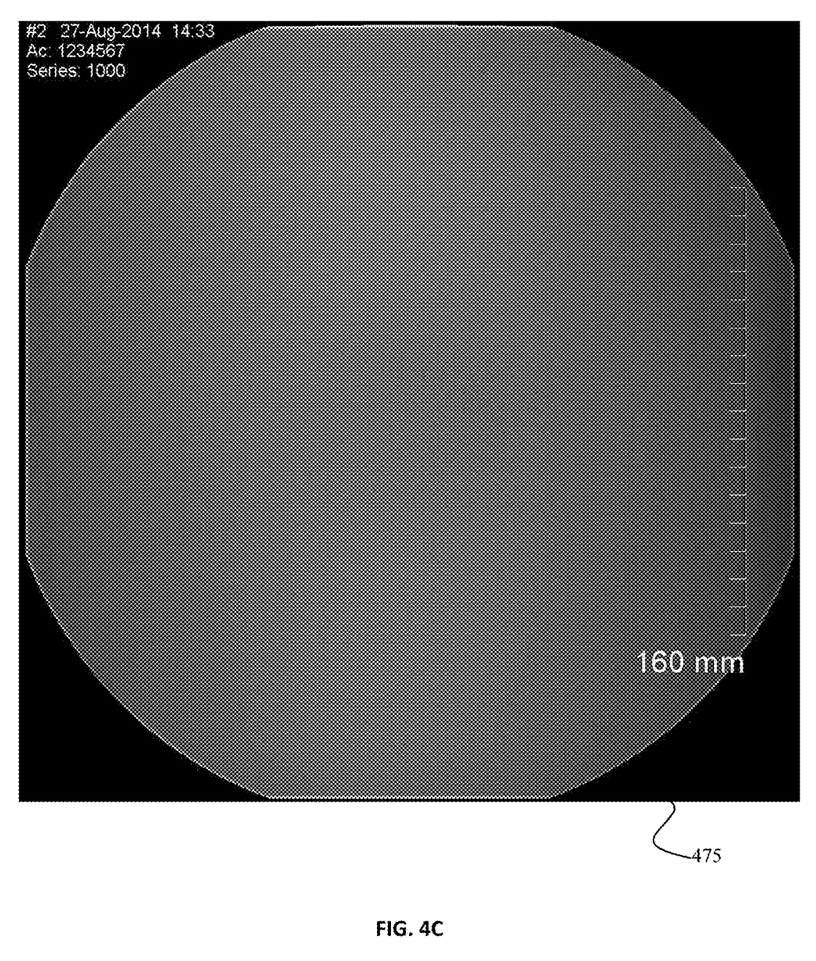
FIG. 4C shows an example x-ray image taken with the foam positioning device, formed using process(es) and/or system(s) disclosed and described herein, without a subject hand in the picture.

FIG. 4C shows an example x-ray image 475 taken with the foam positioning device (e.g., positioner 300) formed using the process 100 and/or system 200 without a subject hand in the picture. As illustrated in the example 475, no artifacts are found.

Modifications and variations as would be apparent to a skilled addressee are determined to be within the scope of the present invention.

It is to be understood that, if any prior art is referred to herein, such reference does not constitute an admission that the prior art forms a part of the common general knowledge of the art in any country.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Several embodiments are described above with reference to the drawings. These drawings illustrate certain details of specific embodiments that implement the systems and methods and programs of the present invention. However, describing the invention with drawings should not be construed as imposing on the invention any limitations associated with features shown in the drawings. It will be understood that the invention disclosed and defined in this specification extends to all alternative combinations of two or more of the individual features mentioned or evident from the text or drawings. All of these different combinations constitute various alternative aspects of the invention.

The invention claimed is:

1. A foam positioner device comprising:
   an outer profile formed at at least a first angle to support a first anatomy to be imaged when positioned by the outer profile of the foam positioner device, wherein the first angle is an angle other than ninety degrees to at least reduce an associated artifact in an image to be obtained of the first anatomy while the first anatomy is supported by the outer profile of the foam positioner device, wherein the first angle divides the outer profile of the device into at least a first portion and a second portion to support first and second parts of the first anatomy to be imaged, wherein no angle of the outer profile is ninety degrees, and wherein the outer profile does not form a ninety degree angle with respect to a surface on which the foam positioner device is to rest, the outer profile to have a length greater than a width to support the first anatomy along the length of the outer profile; and
   a coating covering the outer profile to seal the outer profile of the foam positioner device.

2. The device of claim 1, wherein the first angle includes an angle between 60 degrees and 85 degrees.

3. The device of claim 1, wherein the first angle includes a forty-five degree angle.

4. The device of claim 1, wherein the outer profile is formed according to a plurality of angles including at least the first angle and a second angle, wherein the first angle and the second angle divide the outer profile into at least the first portion, the second portion, and a third portion.

5. The device of claim 1, wherein the coating includes a radiolucent coating.

6. The device of claim 1, wherein the coating includes a waterproof vinyl coating.

7. The device of claim 1, wherein the coating includes a cleanable latex coating.

8. The device of claim 1, wherein the outer profile is formed from a radiolucent foam.

9. The device of claim 8, wherein the radiolucent foam includes at least one of a polyurethane foam, a thermosetting polymer foam, or a thermoplastic polymer foam.

10. The device of claim 1, wherein the first anatomy includes at least one of a hand or a finger.

11. A method of manufacturing a foam positioner device, the method comprising:
    forming an outer profile of the foam positioner device at at least a first angle to support a first anatomy to be imaged when positioned by the outer profile of the foam positioner device, wherein the first angle is an angle other than ninety degrees to at least reduce an associated artifact in an image to be obtained of the first anatomy while the first anatomy is supported by the outer profile of the foam positioner device, wherein the first angle divides the outer profile of the device into at least a first portion and a second portion to support first and second parts of the first anatomy to be imaged, wherein no angle of the outer profile is ninety degrees, and wherein the outer profile does not form a ninety degree angle with respect to a surface on which the foam positioner device is to rest, the outer profile to have a length greater than a width to support the first anatomy along the length of the outer profile; and
    covering the outer profile with a coating to seal the outer profile of the foam positioner device.

12. The method of claim 11, wherein the first angle includes an angle between 60 degrees and 85 degrees.

13. The method of claim 11, wherein the first angle includes a forty-five degree angle.

14. The method of claim 11, wherein forming the outer profile further includes forming the outer profile according to a plurality of angles including at least the first angle and a second angle, wherein the first angle and the second angle divide the outer profile into at least the first portion, the second portion, and a third portion.

15. The method of claim 11, wherein the coating includes at least one of a radiolucent coating, a waterproof vinyl coating, or a cleanable latex coating.

16. The method of claim 11, wherein the outer profile is formed from a radiolucent foam.

17. The method of claim 16, wherein the radiolucent foam includes at least one of a polyurethane foam, a thermosetting polymer few foam, or a thermoplastic polymer foam.

18. The method of claim 11, wherein the first anatomy includes at least one of a hand or a finger.

19. The method of claim 11, further including cutting the outer profile from a foam source material before covering the outer profile with the coating.

20. The method of claim 19, further including sorting the foam positioner device with respect to a plurality of foam positioner devices before covering the outer profile with the coating.

* * * * *